United States Patent [19]

Desmurs

[11] Patent Number: 5,162,565
[45] Date of Patent: Nov. 10, 1992

[54] PROCESS FOR PREPARING DITERTIARY-ALKYL DICARBONATE

[75] Inventor: Jean-Roger Desmurs, Saint Syphorien d'Ozon, France

[73] Assignee: Rhone-Poulenc Chimie, Cedex, France

[21] Appl. No.: 790,028

[22] Filed: Nov. 6, 1991

Related U.S. Application Data

[63] Continuation of Ser. No. 477,523, Feb. 9, 1990, abandoned.

[30] Foreign Application Priority Data

Feb. 10, 1989 [FR] France ................................ 89 01733

[51] Int. Cl.⁵ .............................................. C07C 69/96
[52] U.S. Cl. ................................................... 558/276
[58] Field of Search ........................................ 558/276

[56] References Cited

U.S. PATENT DOCUMENTS 3,562,295  2/1971  Pedersen ............................. 549/352

FOREIGN PATENT DOCUMENTS 2026481  9/1970  France .
2052947  4/1971  France .
2450120  9/1980  France .
 186847  7/1989  Japan ................................... 558/276
 659561  4/1979  U.S.S.R. ............................. 558/276
1304367  1/1973  United Kingdom .

OTHER PUBLICATIONS

J. H. Howe, J. of Org. Chem. 27; 1901–02 (1962).
Pozdev, Smirnova Podgornova, Zentsova and le Kalei Zhurnal Urganicheskoi Khimii, vol. 15; (1): 106–109 (1979) and translated in the Org. Chem. USSR 1979, p. 95 (Translation only provided).

Primary Examiner—Jose G. Dees
Assistant Examiner—Joseph M. Conrad, III
Attorney, Agent, or Firm—Finnegan, Henderson, Farabow, Garrett and Dunner

[57] ABSTRACT

The present invention relates to a novel process for the preparation of a ditertiary-alkyl dicarbonate from an acid halide in the presence of a complexing agent. More particularly, it relates to the preparation of a ditertiary-butyl dicarbonate.

11 Claims, No Drawings

PROCESS FOR PREPARING DITERTIARY-ALKYL DICARBONATE

This application is a continuation of application Ser. No. 07/477,523 filed Feb. 9, 1990 now abandoned.

The invention relates to a novel process for the preparation of a ditertiary-alkyl dicarbonate. More particularly, it relates to the preparation of a ditertiary-butyl dicarbonate from an acid halide.

BACKGROUND OF THE INVENTION

The expression tertiary-alkyl designates a saturated hydrocarbon radical having a tertiary carbon which carries ethyl or methyl radicals independently of one another. If the tertiary carbon carries only methyls, the tertiary-alkyl radical is tertiary-butyl. In the description which follows, only the tertiary-butyl radical will be discussed as an example of the tertiary-alkyls envisaged by the description; however, the use of one example as a means to describe the process is not intended to limit the scope of protection to only one species.

It is well known in the art to prepare ditertiary-butyl dicarbonate, $(BOC)_2O$, from tertiary-butyl carbonate and phosgene, such as described by J. H. Howe in the Journal of Organic Chemistry 27, 1901 (1962). However, industry avoids the use of phosgene due to safety problems.

It is also known to prepare tertiary-butyl dicarbonate by condensing tertiary-butyl carbonate with an acid chloride in a mixture of toluene and dimethylformamide as disclosed by the article published by Pozdev, Smirnova Podgornova, Zentsova and le Kalei in Zhurnal Urganicheskoi Khimii, volume 15, No. 1, pages 106-109, in 1979 and translated in the Journal of Organic Chemistry USSR 1979, page 95. However, when we reproduced these experiments, the yields of tertiary.-butyl dicarbonate obtained were not satisfactory.

SUMMARY OF THE INVENTION

Applicants have discovered a process for preparing dicarbonate in the absence of phosgene and in good yields. The process comprises condensing tertiary-butyl pyrocarbonate with an acid halide in the presence of a complexing agent.

The reaction is represented diagrammatically below:

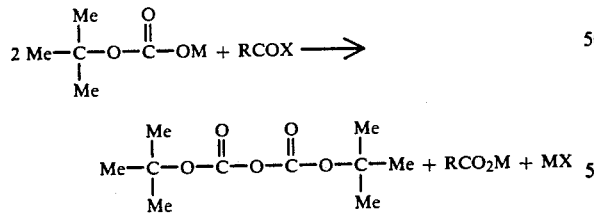

wherein X represents a halogen and M represents an alkali metal.

The tertiary-butyl pyrocarbonate is obtained in any known manner, for example by carbonating a tertiary-butylate. The preferred tertiary-butyl pyrocarbonates, are salts of the alkali metals K, Na, Li and most particularly the sodium salt (M=Na).

The acid halides which are useful in the process of the invention are selected from the chlorides or bromides of carboxylic acids having 1 to 7 carbon atoms and preferably substituted by electron-attracting groups, such as halogen atoms for the aliphatic and aromatic series, and nitro groups for the aromatic series.

Preferred acid halides are carboxylic acid chlorides having 2 carbon atoms. Of these preferred acid halides, trihalogenoacetyl chloride and dihalogenoacetyl chloride are most preferred, the most accessible being dichloroacetyl and trichloroacetyl chlorides.

The sequestering agents are selected from at least 3 classes of complexing agents, comprising the oxygen-containing tertiary amines and the oxygen- or sulfur-containing, cyclic or macrocyclic polyethers.

The first class consist of sequestering agents of formula I:

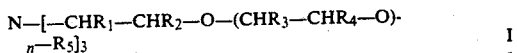

wherein n is an integer greater than or equal to 0 and smaller than or equal to about 10 ($0 \leq n \leq 10$); $R_1$, $R_2$, $R_3$, and $R_4$, which are identical or different, represent a hydrogen atom or an alkyl radical having 1 to 4 carbon atoms; and $R_5$ represents an alkyl or cycloalkyl radical having 1 to 12 carbon atoms, a phenyl radical or a radical of the formula $-C_mH_{2m}-\phi$ or $C_mH_{2m+1}-\phi-$, m being 1 to about 12.

The second class of complexing agents consists of cyclic polyethers having 6 to 30 atoms in the ring, preferably macrocyclic polyethers having 15 to 30 atoms in the ring, and built up from 2 to 10, preferably 4 to 10, $-O-X$ units, in which X is either $-CHR_6-CHR_7-$ or $-CHR_6-CHR_8-CR_9R_7-$, where $R_6$, $R_7$, $R_8$ and $R_9$, which are identical or different, are a hydrogen atom or an alkyl radical having 1 to 4 carbon atoms, and one of the X can be $-CHR_6-CHR_8CR_9R_7-$ if the $-O-X$ units contain the grouping $-O-CHR_6-CHR_7-$.

The third class of complexing agents consists of the compounds of formulas IIa, IIb and IIc:

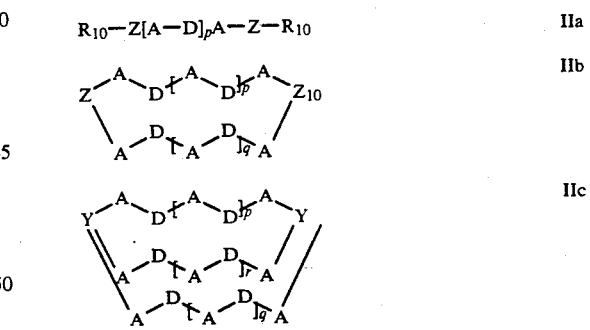

wherein Z represents O or $Y-R_{10}$, Y represents N or P, A represents an alkylene group having 1 to 3 carbon atoms, D represents O, S or $N-R_{11}$ where $R_{11}$ as an alkyl radical having 1 to 6 carbon atoms, $R_{10}$ represents an alkyl radical having 1 to 6 carbon atoms, and p, q and r, which are identical or different, are integers from 1 to 5.

In a preferred embodiment of the process of the invention, at least one sequestering agent of the formula (I) is used wherein $R_1$, $R_2$, $R_3$ and $R_4$ represent a hydrogen atom or a methyl radical, and $R_5$ and n have the meaning as described meaning.

The sequestering agents particularly preferred for use in the process are those wherein n is greater than or equal to 0 and smaller than or equal to 6, and wherein $R_5$ represents an alkyl radical having 1 to 4 carbon atoms.

Examples of sequestering agents suitable for use in the inventive process are:

tris-(3-oxabutyl)-amine of the formula:

N—(CH$_2$—CH$_2$—O—CH$_3$)$_3$ tris-(3-oxaheptyl)-amine of the formula:

N—(CH$_2$—CH$_2$O—C$_4$H$_9$ )$_3$ tris-(3,6-dioxaheptyl)-amine of the formula:

N—(CH$_2$—CH$_2$—O—CH$_2$—CH$_2$—O—CH$_3$)$_3$ tris-(3,6,9-trioxadecyl)-amine of the formula:

N—(CH$_2$CH$_2$—O—CH$_2$—CH$_2$—O—CH$_2$—CH$_2$—O—CH$_3$)$_3$ tris-(3,6-dioxaoctyl)-amine of the formula:

N—(CH$_2$—CH$_2$—O—CH$_2$—CH$_2$—O—C$_2$H$_5$)$_3$ tris-(3,6,9-trioxaundecyl)-amine of the formula:

N—(CH$_2$—CH$_2$—O—CH$_2$—CH$_2$—O—CH$_2$—CH$_2$—O—C$_2$H$_5$)$_3$ tris-(3,6-dioxanonyl)-amine of the formula:

N—(CH$_2$—CH$_2$—O—CH$_2$—CH$_2$—O—C$_3$H$_7$)$_3$ tris-(3,6,9-trioxadodecyl)-amine of the formula:

N—(CH$_2$CH$_2$—O—CH$_2$—CH$_2$—O—CH$_2$—CH$_2$—O—C$_3$H$_7$)$_3$ tris-(3,6-dioxadecyl)-amine of the formula:

N—(CH$_2$—CH$_2$—O—CH$_2$—CH$_2$—O—C$_4$H$_9$)$_3$ tris-(3,6,9-trioxatridecyl)-amine of the formula:
N—(CH$_2$—CH$_2$—O—CH$_2$—CH$_2$—O—CH$_2$—CH$_2$—O—C$_4$H$_9$)$_3$ tris-(3,6,9,12-tetraoxatridecyl)-amine of the formula:

N—(CH$_2$—CH$_2$—O—(CH$_2$—CH$_2$—O—)$_3$—CH$_3$)$_3$ tris-(3,6-dioxa-4-methylheptyl)-amine of the formula:

N—(CH$_2$—CH$_2$—O—CHCH$_3$—CH$_2$—O—CH$_3$)$_3$ tris-(3,6-dioxa-2,4-dimethylheptyl)-amine of the formula:
N—(CH$_2$—CHCH$_3$—O—CHCH$_3$—CH$_2$—O—CH$_3$)$_3$.

The preferred compound of formula I is tris-(dioxaheptyl)amine. The preparation of these sequestering agents is described in French Patent Application No. 2,450,120.

Cyclic ethers useful in the process according to the invention comprise compounds such as dioxane or the macrocyclic ethers known generally "crown ethers", which are described in French Patent No. 2,026,481.

The following are examples of crown ethers which can be used according to the invention:

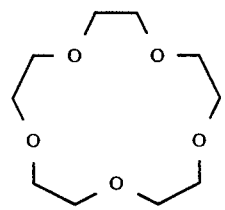

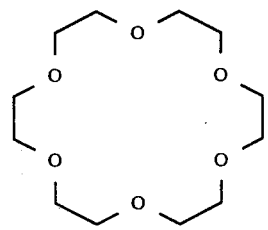

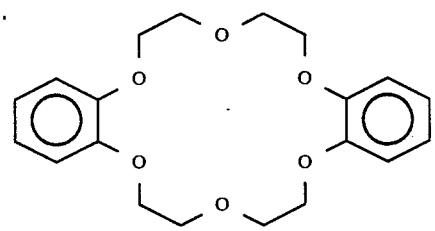

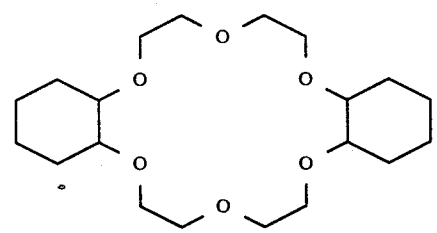

Some of the compounds from the third class of complexing agents are described in French Patent No. 2,052,947.

The following are examples of compounds from this third class suitable for use in the process according to the invention:

CH$_3$—O—CH$_2$—CH$_2$—O—CH$_2$—CH$_2$—OCH$_3$

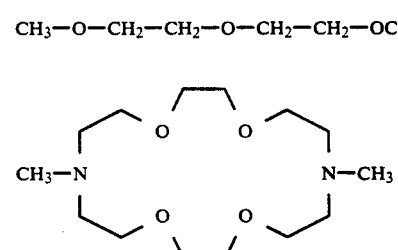

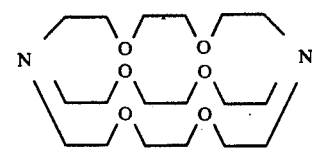

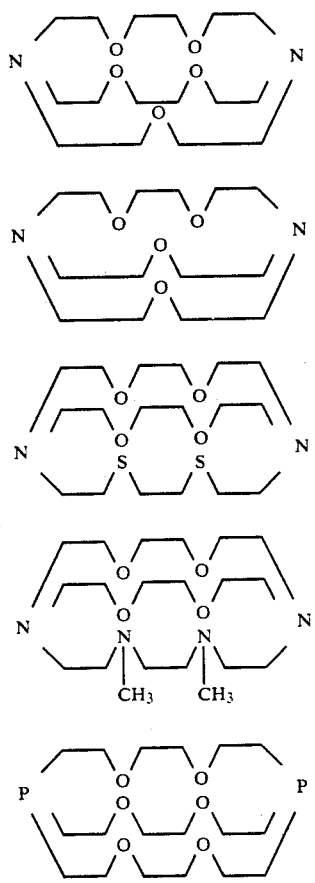

According to a first preferred embodiment Of the invention, sodium tertiary-butylate is contacted with carbon dioxide, then trichloroacetyl chloride is added and subsequently, a supplementary quantity of tertiary-butylate is added.

The complexing agent is introduced at any time, during the carbonating or before the addition of the supplementary quantity of tertiary-butylate.

According to a second preferred embodiment, all the tertiary-butylate is introduced at the start of the reaction, and then the acid chloride is added, whereby the complexing agent is added at any time.

In yet another embodiment of the invention, all the tertiary-butylate is introduced o top of the acid chloride.

The reaction can be carried out in any solvent, whatever the nucleophilic character of the medium. The following solvents are useful in the inventive process.
   aromatic hydrocarbon derivatives such as: benzene, the xylenes and toluene;
   polar aprotic solvents such as: dimethylformamide,
   oxygen-containing solvents such as: dioxane and diethylene and dimethylene glycols.

Generally, the best solvents have a melting point $\leq 10°$ C. and a boiling point $\leq 150°$ C., and are inert towards the reaction mixture and immiscible with water.

Moreover, it is advantageous if the partition coefficients of the complexing agent and the ditertiary-butyl dicarbonate between the organic phase and the aqueous phase are such that the complexing agent passes at least one hundred times more easily into the water than the ditertiary-butyl decarbonate.

Preferred solvents meeting the above limitations are aromatic solvents and petroleum fractions containing at least 50% of aromatics.

Preferably, the molar quantity of acid halide used is between 0.3 and 0.49 times the quantity of tertiary-butylate employed. The reaction temperature is advantageously between $-10°$ C. and $60°$ C.

DETAILED DESCRIPTION OF THE INVENTION

The present invention will be described more completely by reference to the following examples which should not be considered as limiting the invention.

EXAMPLE 1

Standard operating procedure. Influence of the quantity of $TDA_1$ 12.8 g of tBuONa (0.133 mole) and 75 ml of dry toluene were charged to a 250 ml reactor.

At ambient temperature, $CO_2$ was introduced which caused evolution of heat. The introduction was carried out for thirty minutes. The introduction of $CO_2$ was then stopped and the reaction mixture was cooled to 10° C., at which temperature x ml of TDA and then 9.7 g of trichloroacetyl chloride (0.0506 mole) dissolved in 30 ml of toluene, were added for the first time at 10° C. in 10 minutes. The reaction mixture was very thick. The temperature of the reaction mixture was then allowed to rise to ambient temperature and the mixture was then stirred for 5 hours and 30 minutes.

After cooling, 100 ml of ice water were added. After washing with 3×100 ml of water and drying over 15 g of sodium sulfate, the organic phase was evaporated at ambient temperature.

The orange-colored product obtained was analyzed by gas chromatography.

| Experiment | Toluene | Complexing agent | Temperature | Duration | RY |
|---|---|---|---|---|---|
| Comparison | 75 + 30 | — | 25° C. | 5 h 30 | 6 |
| 1 | 75 + 30 | 1 ml of TDA 1 (0.003 mole) | 25° C. | 5 h 30 | 53 |
| 2 | 75 + 30 | 2 ml of TDA 1 | 25° C. | 5 h 30 | 62 |
| 3 | 75 + 30 | 3 ml of TDA 1 | 25° C. | 5 h 30 | 78 |
| 4 | 75 + 30 | 5 ml of TDA 1 | 25° C. | 5 h 30 | 77.5 |

RY is the yield relative to product introduced:
$$\frac{\text{Quantity of product obtained (moles)}}{\text{Quantity of product expected (moles)}}$$

EXAMPLE 2

Influence of Temperature

The procedure of Example 1 was followed, charging 0.13 mole of sodium tertiary-butylate, 0.051 mole of trichloroacetyl chloride (TCAC), 75+30 ml of toluene and 5 ml of TDA 1 (0.0015 mole).

The carbonation was carried out at 10° C. and then, after running in the TCAC, the reaction temperature was taken to the value T given in the table. The duration of the reaction was 5 hours 30 minutes.

| Experiment | Toluene | Complexing agent | Temperature | Duration | RY |
|---|---|---|---|---|---|
| 5 | 75 + 30 | 5 ml of TDA 1 | 10° C. | 5 h 30 | 79 |

-continued

| Experiment | Toluene | Complexing agent | Temperature | Duration | RY |
|---|---|---|---|---|---|
| | | (0.015 mole) | | | |
| 6 | 75 + 30 | 5 ml of TDA 1 | 20° C. | 5 h 30 | 77.5 |
| 7 | 75 + 30 | 5 ml of TDA 1 | 28° C. | 5 h 30 | 76 |
| 8 | 75 + 30 | 5 ml of TDA 1 | 50° C. | 5 h 30 | 77 |

EXAMPLE 3

Influence of the tBuONa/TCAC ratio

The procedure of Example 1 was followed, charging 0.13 mole of sodium tertiary-butylate (tBuONa), x moles of trichloroacetyl chloride (TCAC), 75+30 ml of toluene and 0.015 mole of TDA 1. The reaction was carried out for 5 hours and 30 minutes at 20°.

| Experiment | Toluene | Moles of TCAC | Excess of tBuONa over the stoichiometric amount | Temperature | RY |
|---|---|---|---|---|---|
| 9 | 75 + 30 | 0.065 | 0 | 20° C. | 52.5 |
| 10 | 75 + 30 | 0.062 | 4% | 20° C. | 79.5 |
| 11 | 75 + 30 | 0.059 | 9% | 20° C. | 80.5 |
| 12 | 75 + 30 | 0.051 | 21% | 20° C. | 77.5 |

EXAMPLE 4

Influence of the Duration

The procedure of Example 1 was followed, charging 0.13 mole of sodium tertiary-butylate, 0.51 mole of trichloroacetyl chloride, x+30 ml of toluene and 0.015 mole of TDA 1. The reaction was carried out for 5 hours 30 minutes at 20° C.

| Experiment | Toluene | Temperature | RY |
|---|---|---|---|
| 13 | 35 + 30 | 20° C. | 37 |
| 14 | 75 + 30 | 20° C. | 77.5 |
| 15 | 180 + 30 | 20° C. | 82 |
| 16 | 290 + 30 | 20° C. | 77 |

EXAMPLE 5

Influence of Duration

The procedure of Example 1 was followed. In the comparative experiments, 0.13 mole of sodium tertiary-butylate, 10 ml of DMF (at the end of carbonation), 0.051 mole of trichloroacetyl chloride and 75+30 ml of toluene were charged. The reaction was carried out at 20° for a variable time.

| Experiment | Toluene | Complexing solvent | Temperature | Duration | RY |
|---|---|---|---|---|---|
| Comparison with the publication by POZDEV, using toluene + DMF | 75 + 30 | DMF 10 ml | 10° C. | 1 h | 9% |
| Comparison with the publication by POZDEV, using toluene + DMF | 75 + 30 | DMF 10 ml | 20° C. | 3 h 30 | 42% |
| Comparison with the publication by POZDEV, using toluene + DMF | 75 + 30 | DMF 10 ml | 20° C. | 5 h 30 | 51% |
| Comparison with the publication by POZDEV, using toluene + DMF | 75 + 30 | DMF 10 ml | 20° C. | 16 h | 57.3% |

The experiments were carried out with 0.13 mole of sodium tertiary-butylate, 0.051 mole of trichloroacetyl chloride, 75+30 ml of toluene and 0.015 mole of TDA 1 at a temperature of 20° C.

| Experiment | Toluene | Complexing agent | Temperature | Duration | RY |
|---|---|---|---|---|---|
| 17 | 75 + 30 | 5 ml of TDA 1 | 20° C. | 1 h | 76 |
| 18 | 75 + 30 | 5 ml of TDA 1 | 20° C. | 1 h 45 | 82 |
| 19 | 75 + 30 | 5 ml of TDA 1 | 20° C. | 5 h 30 | 77.5 |
| 20 | 75 + 30 | 5 ml of TDA 1 | 20° C. | 22 h 30 | 75 |

EXAMPLE 6

Influence of the Solvent

The procedure of Example 1 was followed, charging 0.13 mole of tBuONa, 0.051 mole of TCAC when appropriate, 0.015 mole of TDA 1 and 75+30 ml of a solvent.

| Experiment | Solvent | Complexing agent | Temperature | Duration | RY |
|---|---|---|---|---|---|
| Comparison | Toluene (75 + 30) | | 20° C. | 5 h 30 | 6% |
| 4 | Toluene (75 + 30) | 5 ml of TDA 1 | 20° C. | 5 h 30 | 77.5% |
| 21 | Dioxane (75 + 30) | | 20° C. | 5 h 30 | 23 |
| 22 | Dioxane (75 + 30) | 5 ml of TDA 1 | 20° C. | 5 h 30 | 69% |
| 23 | Diglyme (75 + 30) | | 20° C. | 5 h 30 | 40% |

EXAMPLE 7

Influence of the Complexing Agent

The procedure of Example 1 was followed, with 0.13 mole of tBuONa, x moles of a complexing agent, 0.051 mole of TCAC and 75+30 ml of toluene.

| Experiment | Toluene | Complexing agent | Temperature | Duration | RY |
|---|---|---|---|---|---|
| Comparative | 75 + 30 | | 20° C. | 5 h 30 | 6% |
| 24 | 75 + 30 | Diglyme (0.13 mole) | 20° C. | 5 h 30 | 43% |
| 25 | 75 + 30 | Dioxane | 20° C. | 5 h 30 | 14% |

-continued

| Experiment | Toluene | Complexing agent | Temperature | Duration | RY |
|---|---|---|---|---|---|
| | | (0.23 mole) | | | |

EXAMPLE 8

Influence of the Acid Halide

The procedure of Example 1 was followed, with 0.13 mole of tBuONa, 0.051 mole of acid chloride, 75+30 ml of toluene and 0.015 mole of TDA at a temperature of 20° C. for 5 hours 30 minutes.

| Experiment | Toluene | Acid chloride | Temperature | Duration | RY |
|---|---|---|---|---|---|
| 26 | 75 + 30 | CCl$_3$COCl | 20° C. | 5 h 30 | 77.5% |
| 27 | 75 + 30 | CHCL$_2$COCl | 20° C. | 5 h 30 | 5% |
| 28 | 75 + 30 | CH$_2$ClCoCl | 20° C. | 5 h 30 | 5% |

EXAMPLE 9

Change of Substrate

Ditertiary-amyl carbonate 8.1 g of sodium t-amylate (0.064 mole), 100 ml of toluene and 5 g of TDA 1 were introduced into a 250 ml reactor. CO$_2$ was injected into this suspension for 30 minutes, until the exit rate from the reactor was identical to the inlet rate. After cooling to 0° C., 3.8 g of dichloroacetyl chloride (0.0258 mole) were run within 10 minutes. The reaction mixture was then heated again to 20°, where it was stirred for five hours. After washing, the organic phase was dried and evaporated. 1.7 g of an aqueous product were recovered, in which NMR analysis gave 88% of ditertiary-amyl carbonate, corresponding to a relative yield of 23.5% based on dichloroacetyl chloride employed.

I claim:

1. A process for preparing a ditertiary-alkyl dicarbonate, which comprises contacting a tertiary-alkyl carbonate and an acid halide in the presence of a complexing agent selected from the following three types of complexing agents:

1) oxygen-containing tertiary amines corresponding to the formula:

N[CHR$_1$13
    CHR$_2$—O—(CHR$_3$—CHR$_4$—O)$_n$—R$_5$]$_3$ wherein n is an integer greater than or equal to 0 and smaller than or equal to about 10 (0≦n≦10); wherein R$_1$, R$_2$, R$_3$ and R$_4$ are identical or different and represent a hydrogen atom or an alkyl radical having 1 to 4 carbon atoms, and R$_5$ represents an alkyl or cycloalkyl radical having 1 to 12 carbon atoms, a phenyl radical or a radical of the formula —C$_m$H$_{2m}$—φ or C$_m$H$_{2m-1}$—φ—, m being 1 to about 12;

2) cyclic ethers having 6 to 30 atoms in the ring and built up from 2 to 10 —O—X units in which X is either —CHR$_6$—CHR$_7$— or —CHR$_6$—CHR$_8$—CR$_9$R$_7$—, where R$_6$, R$_7$, R$_8$ and R$_9$, which are identical or different, are a hydrogen atom or an alkyl or an alkyl radical having 1 to 4 carbon atoms, and one of the X can be —CHR$_6$—CHR$_8$CR$_9$R$_7$— if the —O—X units contain the grouping —O—CHR$_6$—CHR$_7$—; or 3) compounds of formulas IIa, IIb or IIc:

  IIa

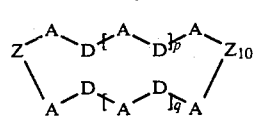  IIb

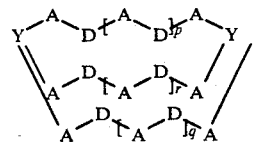  IIc wherein Z represents O or Y—R$_{10}$; Y represents N or P; A represents an alkylene group having 1 to 3 carbon atoms; D represents O, S or N—R$_{11}$, where R$_{11}$ is an alkyl radical having 1 to 6 carbon atoms; R$_{10}$ is an alkyl radical having 1 to 6 carbon atoms; and p, q and r, are identical or different, and are integers from 1 to 5.

2. The process as claimed in claim 1, wherein the tertiary-alkyl pyrocarbonate is a sodium salt.

3. The process as claimed in claim 1, wherein the acid halide is trichloroacetyl chloride or dichloroacetyl chloride.

4. The process as claimed in claim 1, wherein the complexing agent is a macrocyclic ether having 15 to 30 atoms in the ring.

5. The process as claimed in claim 1, wherein the complexing agent is a cyclic ether built up from 4 to 10 —O—X units.

6. The process as claimed in claim 1, wherein the complexing agent is trisdioxaheptylamine.

7. The process as claimed in claim 1, wherein the complexing agent is the dimethyl ether of diethylene glycol.

8. The process as claimed in claim 1, wherein the complexing agent is the dimethyl ether of diethylene glycol.

9. The process as claimed in claim 1, wherein the complexing agent is dioxane.

10. The process according to claim 1, wherein the reaction is carried out in an aromatic solvent.

11. The process according to claim 10, wherein the aromatic solvent is toluene.

* * * * *

UNITED STATES PATENT AND TRADEMARK OFFICE
CERTIFICATE OF CORRECTION

PATENT NO.   : 5,162,565
DATED        : November 10, 1992
INVENTOR(S)  : Jean-Roger Desmurs It is certified that error appears in the above-identified patent and that said Letters Patent is hereby corrected as shown below:

Claim 1, Column 9, Line 50 (first line of formula), change "$N[CHR_1 13$" to --$N[CHR_1-$ --; and Signed and Sealed this Fifth Day of April, 1994

Attest:

Attesting Officer

BRUCE LEHMAN

Commissioner of Patents and Trademarks